United States Patent [19]

Bystryak

[11] Patent Number: 5,776,703
[45] Date of Patent: Jul. 7, 1998

[54] IMMUNOASSAY

[76] Inventor: Seymon Bystryak, 62, Hagibor Haalmoni St., Tel-Aviv, Israel, 67222

[21] Appl. No.: 580,397

[22] Filed: Mar. 2, 1995

Related U.S. Application Data

[63] Continuation of Ser. No. 10,705, Jan. 29, 1993, abandoned.

[30] Foreign Application Priority Data

Jan. 31, 1992 [IL] Israel ........................................ 100841

[51] Int. Cl.$^6$ .............................. C12Q 1/26; G01N 33/53
[52] U.S. Cl. ..................... 435/7.9; 435/7.92; 435/28; 436/164; 436/172
[58] Field of Search ..................... 435/25, 28, 810, 435/7.92, 7.9; 436/66, 64, 86, 164, 172, 518

[56] References Cited

U.S. PATENT DOCUMENTS

| | | | |
|---|---|---|---|
| 4,235,792 | 11/1980 | Hsia et al. | 554/81 |
| 5,017,475 | 5/1991 | Harte et al. | 435/7.9 |
| 5,168,047 | 12/1992 | Kondo et al. | 435/28 |

OTHER PUBLICATIONS

Harlow et al (1988) Antivoda A Laboratory Manual Cold Proc. Harbor Press pp. 558 579–581.
Bystrak et al (1992) 202 390–393.
Mekler et al (1992) Anal Chim Acta 264 359–363.
Baeyens et al (1989) J. Pharm. Biomed Anal. 7 1385–1394.
Schler et al (1989) J. Immunological Methods 116 27–19.
Bethesda Research Laboratories 1988 Catalysis p. 120.
Harlow et al (1988) Antibodies: A Laboratory Manual. ColdSpring Harbor Press. pp. 558 579–581.
Bystrak et al (1992) Anal. Biochem. 202 390–393.
Mekler et al (1992) Anal. Chim. Acta 264 359–363.
Baeyens et al (1989) J. Pharm. Biomed. Anal. 7 1385–1394.
Schaler et al (1989) J. Immunological Methods 116:27–29.
Bethesda Research Laboratories 1988 Catalogs p. 120.

*Primary Examiner*—Eric Grimes
*Attorney, Agent, or Firm*—Evenson, McKeown, Edwards & Lenahan P.L.L.C.

[57] ABSTRACT

There is provided an assay of enhanced sensitivity for the qualitative and quantitative determination of haptens. These may be assayed entities such as antigens, antibodies, a wide variety of biologically active proteins. The novel assay of increased sensitivity is based on the formation of a complex of the entity to be measured with another entity, tagging this conjugate with a oxidizing entity, reacting the resultant entity with a redox substrate to form a product which is photosensitive and irradiating same thus enhancing the sensitivity of the assay. Colored or fluorescent products give highly sensitive results. According to a preferred embodiment the oxidized entity is reacted with a non-ionic detergent, enhancing the resulting fluorescence.

11 Claims, 7 Drawing Sheets

IMMUNOASSAY

This is a continuation application of Ser. No. 08/010,705, filed on Jan. 29, 1993, now abandoned.

TECHNICAL FIELD OF INVENTION

The invention relates to a class of immuno-diagnostics in which redoxy reaction takes place.

BACKGROUND OF THE INVENTION

An important part of present day diagnostics is based on antigen-antibody reaction and subsequent detection and measuring the level of labelled antibodies to a suspected antigen. To the antibody or the antigen various labels are attached: radioactive materials, enzymes, dyes and other materials that cause colorimetric or fluorescent effects and so on. Then the level of antibody or antigen concentration is deduced from measurement of the particular label by a method that corresponds it, i.e., radioactive counting, spectrophotometry, fluorescence, colorimetry and other procedures.

The practical application of immunochemical reactions is dependent on the detection sensitivity, i.e. on the threshold concentration of analyte in biological medium such as blood or serum. Higher sensitivity would usually improve the chance of detection of a pathological state in an earlier stage, thus providing for better cure probability, or, alternatively, lessen the quantity of chemical reagents needed for performing a test and thus decreasing its cost.

A broad class of immunochemical reactions used in diagnosis employs enzymes for labelling. Such enzymes then participate as catalysts in the substrate reaction to give a visible color result which is quantitatively read by a spectrophotometer. In this sub-class the enzyme horseradish peroxidase (HRP) and the redoxy substrates such as ortho-phenylenediamine (o-PD) and 3-methyl-2 benzothiazoline hydrazone (MBTA) with 3 (dimethylamino) benzoic acid (DMAB) among many others are very widely used. For instance HRP and o-PD are employed in the detection of carcinoembryonic antigen [CEA], hepatitis-B, myoglobin, HIV-1, HIV-2, insulin and many other antigens.

Another important class uses dye labels of antibodies and antigens which are eventually read by polarization and intensity fluorescence.

The reaction sensitivity depends on a variety of factors and on the effectivity of the major participants in it: antibody, antigen, labelling substance, the end material. According to the invention has established that in many instances the redoxy reaction can be made photosensitive, provided that certain well defined conditions are met, and subsequently the thus acquired photosensitivity serves as amplifier of the reaction, i.e. provides a much improved diagnostic sensitivity.

Some diagnostic procedures measure fluorescence of reaction product by a fluorometer and determine the quantity of the antigen from the value of the fluorometer reading. For this to take place, the reaction product must have, or be made to have measurable fluorescence properties. In many instances the sensitivity of fluorescent procedures is much higher than that of other detection methods.

There are well known methods for enhancing fluorescence of some chemical reaction products. Application of such known methods to the o-PD reaction product does not produce any significant fluorescence. It has now been established that if some of the reaction conditions that are mandatory in the photochemically enhanced redoxy reaction are applied together with these known methods of fluorescence enhancement, the reaction becomes highly fluorescent. The fluorescence so achieved provides for sensitivity similar to that of photochemically enhanced o-PD reaction, namely substantially greater than that of a non-enhanced reaction.

DISCLOSURE OF INVENTION

It is widely known that some chemical reactions are photo sensitive. Such photosensitivity or lack of it stems from the quantum chemical structure and properties of reactants. The rate of a photo sensitive reaction is much higher if the reaction mixture is illuminated by an intense light of a specific wavelength than in a similar reaction taking place in the absence of such light. Consequently, if a reaction taking place in a diagnostic assay can be made photosensitive, the sensitivity of such assay can be substantially enhanced.

In one embodiment of diagnostic assays of the invention relates, an antibody to a suspected antigen is labeled with an enzyme such as HRP and added to a biological liquid, for example blood or serum. A part of the added HRP labelled antibodies binds with the antibodies to the specific antigen existing already in the biological liquid to form an [antibody]-[antigen]-[HRP labelled antibody] complex. Subsequently, after an incubation time, the HRP labelled antibody which did not bind to the Ab-Ag complex is removed from the solution by rinsing. Then, a substrate solution, for instance, $H_2O_2$ and o-PD is added to the test tube; o-PD is oxidized with HRP acting as oxidizing catalyst. The oxidation product in the event of HRP and o-PD is diaminophenazine [DAP]. DAP is a colored substance, the optical density of which is read with the aid of photometer. The result is proportional to HRP bound to antibodies and therefore to the added antibodies forming the Ab-Ag-Ab complex. The known procedure is performed under room light, or preferably in darkness.

If the steps of the procedure taken so far are modified according to the inventive procedure described later the sensitivity can be enhanced by application of intense light at the wavelength of 400 to 500 nm (FIG. 1) which corresponds to the absorption spectrum of the DAP molecule. Thus, but prior to spectrophotometer reading, the test tube is illuminated by an intense source of light of a wavelength in the above range. The DAP obtained in the first stage of reaction together with the light photons serve as new catalyzing agents for further production of DAP. Thus a two stage reaction takes place:

  (1)

  (2)

The resulting optical density of DAP is measured by a spectrophotometer.

To achieve the benefit of photo-enhanced sensitivity special care must be taken in respect of non specific antibody binding and o-PD impurities. All procedures of measurement involve certain imprecision. Such imprecision is dealt with usually by defining the effective measurement threshold and by designating the phenomena taking place below such threshold "noise". In moving from a less precise, in this case less sensitive, procedure to one which is more precise or sensitive, it is necessary to pay particular attention to this region of "noise", which must be carefully analyzed and at least partially removed in order to achieve optimal reaction conditions.

The HRP labelled antibodies bind not only to form Ab—Ag—Ab complexes, they also bind to test tube or equivalent device walls and beads and are not washed out during the rinsing. Therefore, although they are not a part of antigen complex, they appear as if they were and thus distort the results of the detection procedure. In the inventive procedure rinsing is not done by water only; it is accomplished with solutions that contain some of the following substances in various combinations: gelatin, detergents, polymers, proteins or biological liquids containing proteins, lipids and surface active substances.

Since o-PD is a strong reduction agent it may contain some DAP in its "pure" state, i.e. as commercially available material. This residual DAP appears as if it were a product of the HRP catalyzed o-PD oxidation and thus distorts the read value of HRP and consequently that of the detected antibody. To obtain the maximum advantage of the photo enhanced sensitivity high purity o-PD should be used, or alternatively o-PD commercially available as independent material or as a part of a diagnostic kit should be purified.

The sensitivity increase obtained by using a procedure according to the invention, where the commercially available diagnostic kits were used as reference, were at least by a factor of 10, and in some instances as much as 50 times in comparison with these kits.

Many other redoxy reactions and their products used in enzymatic labelling in immuno diagnostics could be amplified photochemically. Another substrate used with HRP is a mixture of MBTA and DMAB is known to be photosensitive. In the conventional immunodiagnostics this is considered a harmful property. According to the inventive procedure it can be used for improved sensitivity.

Since the partial removal of the unbound antibodies and the purification of o-PD proved to be very important in achieving the increase of sensitivity, a version of the new diagnostic assay was tested and subsequently developed for fluorescence reading in lieu of colorometric photochemically enhanced method. In this procedure instead of light illumination or after carrying out the photochemical amplification, detergents favorable to fluorescence were added to the solution. Instead or in addition to detergents other fluorescence enhancing substances may be used. Under these conditions DAP was found to be highly fluorescent (the peak is at 550 nm; see FIG. 5) and the sensitivity was similar to that obtained by the photochemically amplified method with colorimetric detection.

Certain dyes, for instance derivatives of fluorescein and rhodamine are used in labelling of antibodies and antigens. Subsequently, the resulting fluorescence serves as an indicator of antigen or antibody concentration in the solution under investigation. The innovative procedure uses different dyes, such as derivatives of erythrosine and of eozine, methylene blue, Bengal rose, and many others, as labels. Under conditions prescribed by the innovative procedure reaction between such dye and selected substrate is photochemical and takes place only under irradiation of defined wavelength. The reaction produces a colorometric effect which is then read by a spectrophotometer. In certain instances the reaction produces a fluorometric effect which is read by fluorometer. There is a principal difference between the known fluorescence dye diagnostic procedure and the innovative procedure. In the known procedure the dye is strongly fluorescent ab initio. In the innovative procedure the dye in at most weakly fluorescent, and the fluorescence stems either from the label-substrate reaction product or from the substrate. Sometimes the concentration of the measured antibody or antigen is measured by decrease of fluorescence.

The dye labelled innovative procedure may be executed in a homogenous solution. In such version membranes or membrane models, such as liposomes are dissolved in water and serve as a collection site for antibodies and substrate which bind to it hydrophobically. The substrate is in principle any substance which can efficiently react with molecular oxygen in quantum singlet, i.e. excited state, for instance diphenylisobenzofurane and derives of anthracene.

BRIEF DESCRIPTION OF THE FIGURES

The invention is illustrated with references to the enclosed Figures in which.

DETAILED DESCRIPTION OF THE INVENTION

The first phase of the both the enhanced photo sensitive and fluorescent assays conducted in darkness is similar to known methods of detection of antibodies to a suspected antigen in biological solutions such as ELISA (Enzyme Linked Immunosorbent Assay).

The washing step is different. The washing solution contains 1% gelatin, 0.2M NaCl, 2 mM EDTA, 0.1% TRITON X-100 (octylphenoxy polyethoxyethanol) in 0.05M Tris-HCl buffer of ph 7.0. Preventing of non-specific binding of antibodies may be achieved with other solutions which contain different combinations of the following reagents: detergents, polymers, proteins or biological liquids containing proteins such as sera, gelatin, lipids, and surface active substances. Incubation for 40 minutes in the bead test tube is followed by washing of the distillate. The step is repeated three 3 times.

Figure 1:
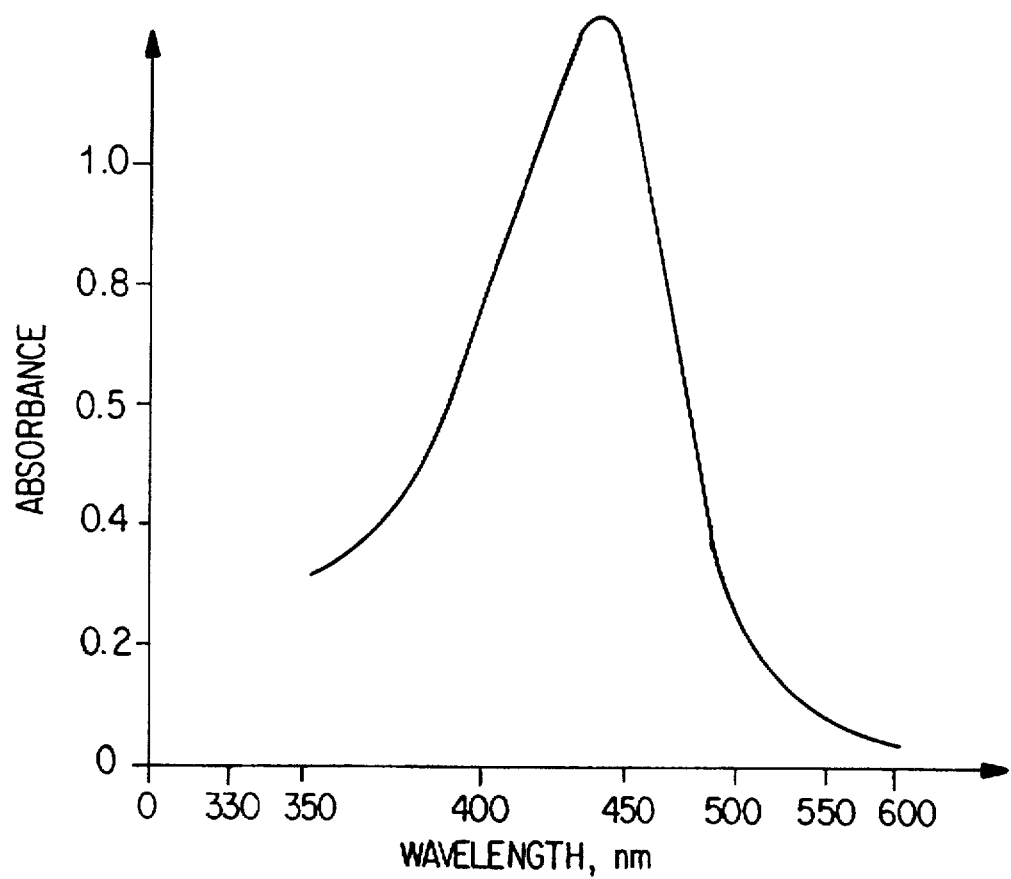
FIG. 1 is a plot of the absorbance of DAP as the function of wavelength.
Figure 2:
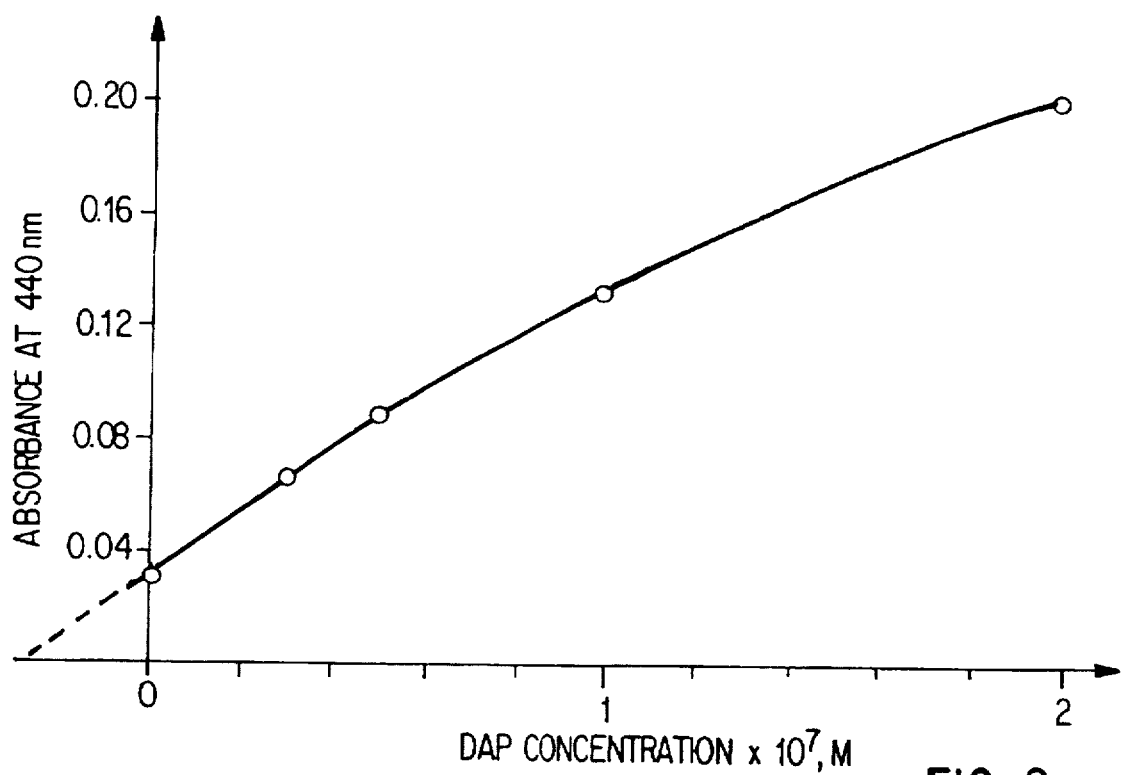
FIG. 2 is a plot of the absorbance of DAP at the wavelength of 440 nm as a function of DAP molar concentration. According to this figure the absorbance at 0 concentration is a positive number: 0.04M—the "background noise."

To determine the significance of o-PD purity the rate and the quantities of non-catalytic DAP formation in a substrate solution were measured (FIG. 2). Commercially available standard o-PD was purified by vacuum sublimation and dissolved in a 0.1M phosphate-citric acid buffer at ph 5.0 ($[\text{-o-PD}]=4\times10^{-3}$M, $[H_2O_2]=5\times10^{-3}$M). Different quantities of DAP primer ($DAP^0$) were added to the substrate solution immediately upon o-PD dissolving. Incubation for 20 minutes was followed by 5 min irradiation by visible light of wavelength of about 440 nm (FIG. 1). By interpolation, the optical density value, $D_{440}$ at no DAP prime added, $[DAP_0]$ =0, corresponds to presence of $3\times10^{-4}$M of DAP, i.e. some DAP concentration was present in the solution before adding of the primer and before the irradiation. The optical density of $3\times10^{-3}$M DAP in a 1 cm wide cuvette is $6.3\times10^{-4}$, a value below the measurement range of common laboratory spectrophotometer. To obtain values which are within common spectrophotometer range, substrate solution incubation time was increased and it was incubated for several hours. The average rate of DAP formation measured by spectrophotometer was $1.1\times10^{-7}$M DAP/hour. After the fluorescent version of the invention was perfected, the results were repeated and confirmed by it a much simpler manner.

The o-PD used in the assay must be of high purity. Commercially available standard o-PD or 0-PD provided in commercially available diagnostic kits can be purified to a sufficient degree. Such purification is attained by vacuum sublimation at $10^{-3}$ mm Hg at 70° C., by passing the o-PD through active charcoal, Sephadex or silica gel medium, by recrystallization and by other methods.

The high purity o-PD is added to the solution and the reaction time allowed for this stage is similar to the time in the parallel step taken by the known methods, it varies from one Ag-Ab complex to another and is in the range of 30 minutes.

In the photo sensitive assay version, the test tube is irradiated with a 1,000 Watts Hg lamp for about 4 minutes. Five mm thick glass filters are used to detain light at wavelength below 410 nm and above 500 nm. Subsequently the reaction is stopped by adding an 2 ml 0.1M sulfuric acid. The final result is read by a spectrophotometer.

In the fluorescence version TRITON X-100 (octylphenoxy polyethoxyethanol) is added to the test tube until detergent concentration of 2% is attained. Immediately following that the result is read by a fluorometer.

In the labelled dye version a system of liposomes, such as dimyristoylphosphatidylecholine, antibodies labelled with erytrozineisothiocyanate, in concentration of $10^{-7}$M, and substrate, such as diphenylisonbenzofurane is prepared. A series of different quantities of antigen to be measured are added. The tubes are then illuminated by strong light from 1,000 watts Hg source at wavelength of about 540 nm, depending on the dye label, for several minutes. The variation in fluorescence as a function of antigen concentration is measured by fluorometer and a calibration curve obtained. After the calibration curve has been obtained the procedure is repeated with a sample of biological solution with an unknown quantity of antigen.

EXAMPLE 1

Colorometric Determination of HRP Concentration in Solution

Figure 3A:
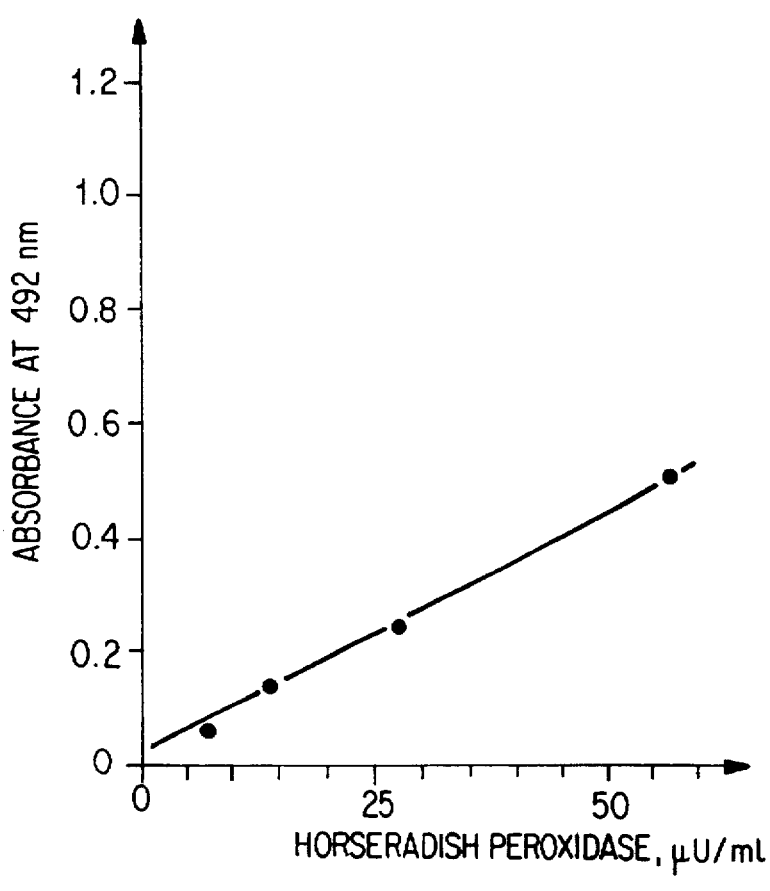
FIG. 3a is a plot of the absorbance of DAP at wavelength of 492 nm as a function of HRP activity in buffer solution without photosensitive amplification.
Figure 3B:
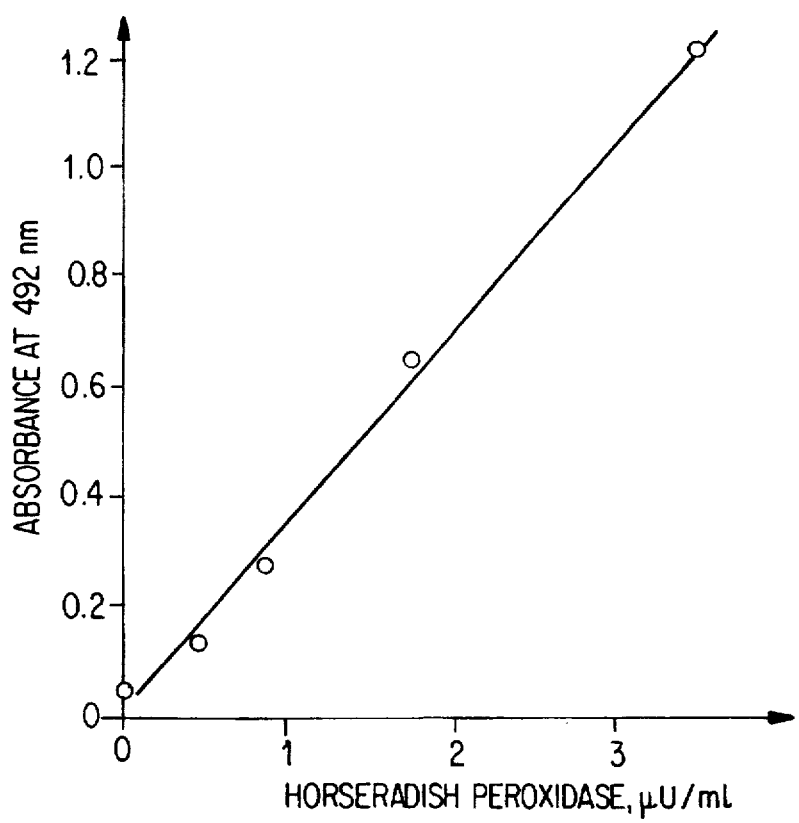
FIG. 3b is a plot of the absorbance of DAP at wavelength of 492 nm as a function of HRP activity in buffer solution with photosensitive amplification.

Horseradish peroxidase was used with stated activity of 250 U/mg proteins, citric acid, Tris and guaiacol and $Na_2HPO_4$. O-PD was purified by vacuum sublimation at $10^{-3}$ mm Hg and 70° C. The activity of HRP was standardized by spectrophotometric method with guaiacol. The HRP mediated oxidation of o-PD was carried out at room temperature in 0.1M phosphate—citric acid buffer at ph 5.0, $[\text{-o-PD}]=4\times10^{-3}$, $[H_2O_2]=5\times10^{-3}$. The substrate solution was used immediately after o-PD dissolution. The reaction time was 30 minutes in every concentration of HRP. In the second stage samples containing different quantities of HRP were irradiated with a 1,000 watts Hg lamp for 4 minutes in a 1 cm cuvette. The stability of irradiation, measured with thermoradiometer was 2%. Five mm thick glass filters were used to filter out light at wavelengths below 410 nm and above 500 nm. The irradiated solution was contained in the cuvette, while HRP was assayed in a buffer. After irradiation, 2 ml of 0.5M sulfuric acid was added. The DAP concentration was 50 times higher than the one obtained conventionally (FIG. 3a and 3b). As to the lower detection limit of HRP, its value was about 0.5 µU/ml, whereas in the convectional method it is about 7 µU/mL.

EXAMPLE 2

Colorometric Determination of Carcinoembryonic Antigen (CEA)

To obtain the calibration curve commercially available Roche CEA ELISA kit was used. The kit contained beads coated with anti-CEA antibody, a set of CEA standard concentration solutions (A), a solution of HRP labeled anti-CEA antibody (B) and serum solution.

Fifty micro-liters of solution A and 200 micro-liters of solution B were added to a test tube containing antibody coated beads. The mixture was incubated for 1 hour at 37° C. Subsequently the beads were rinsed with distilled water. Then o-PD Roche tablets and 0.25 ml of buffer solution were added. The reaction was terminated with 2 ml 0.5M sulfuric acid after 30 minutes. The optical densities were measured at 492 nm. A human blood serum sample was taken and divided into two parts. The concentration of CEA in the first part of the sample (50 micro liters) was measured according to the Roche kit instruction. The experiment is done in essentially the same manner as the calibration curve is obtained. The result was evaluated against the obtained calibration curve and concentration of CEA was found to be 2.5 ng/ml.

Figure 4A:
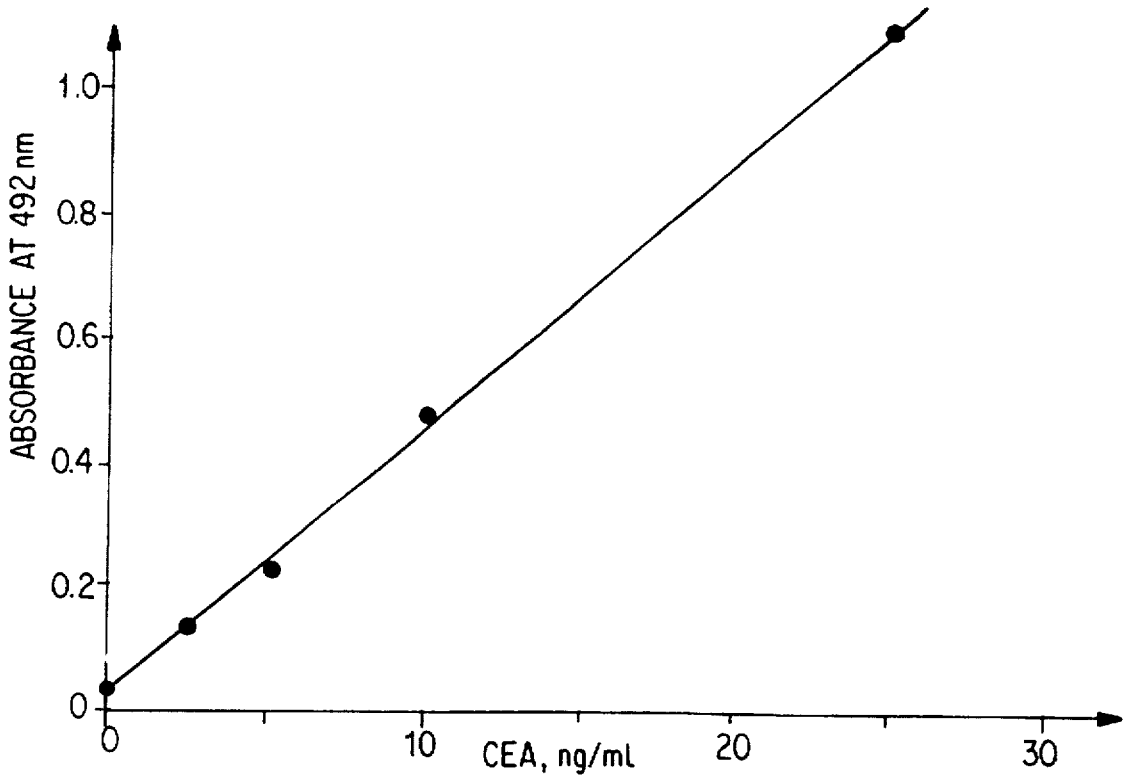
FIG. 4a is a plot of the absorbance of DAP at wavelength of 492 nm as a function of CEA concentration in serum without photosensitive amplification.
Figure 4B:
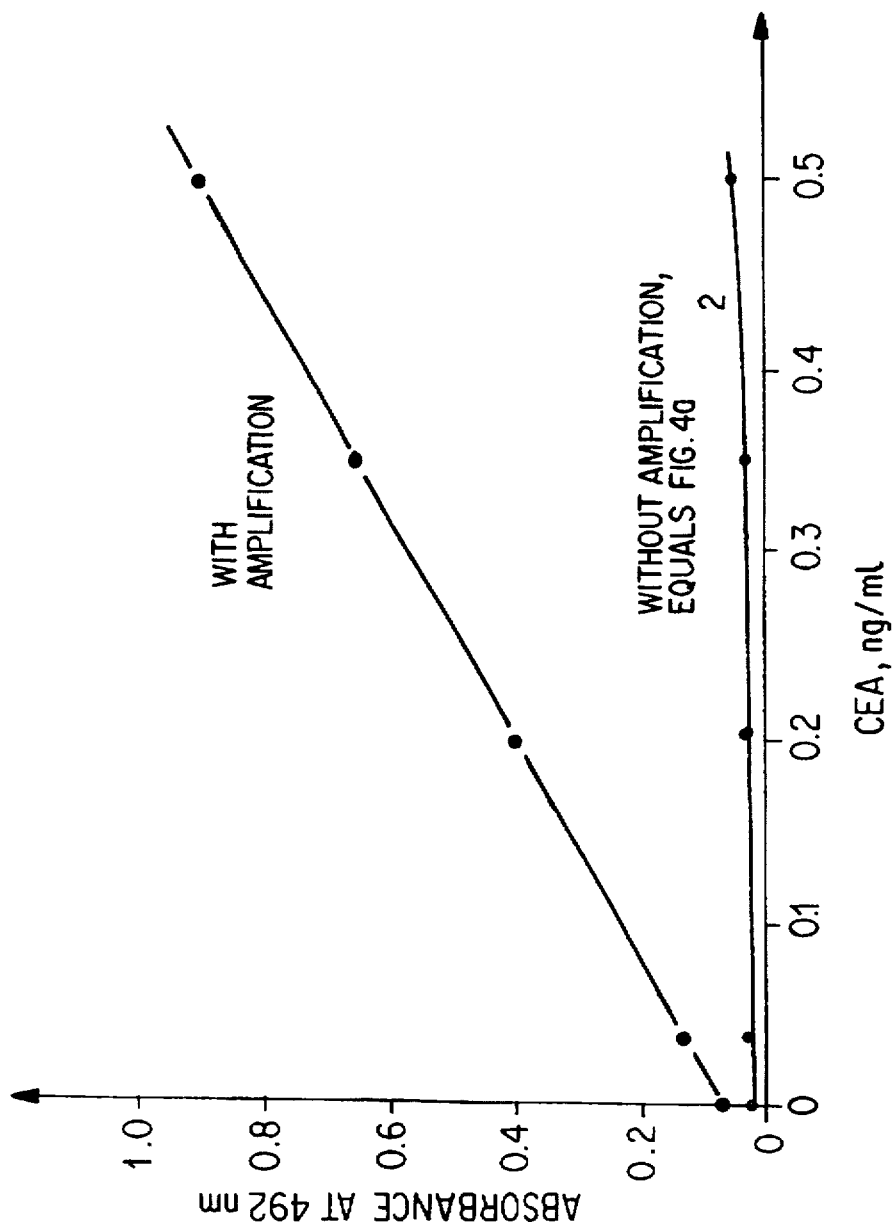
FIG. 4b is a plot of the absorbance of DAP at wavelength of 492 nm as a function of CEA concentration in serum with photosensitive amplification (the chart of FIG. 4a is superimposed for comparison [2]).
Figure 5:
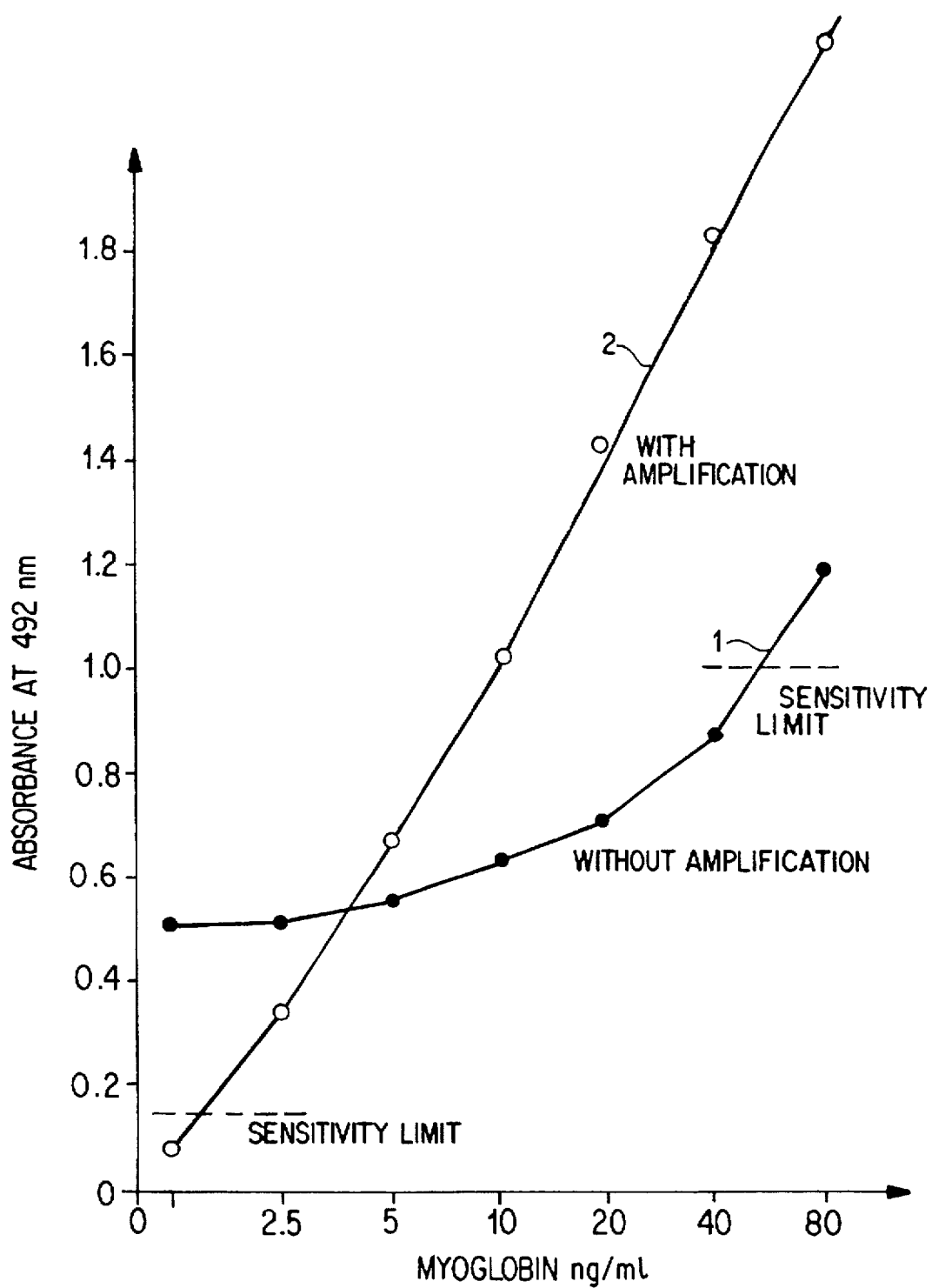
FIG. 5 is a plot of the absorbance of DAP as a function of myoglobin concentration without and with photosensitive amplification.
Figure 6:
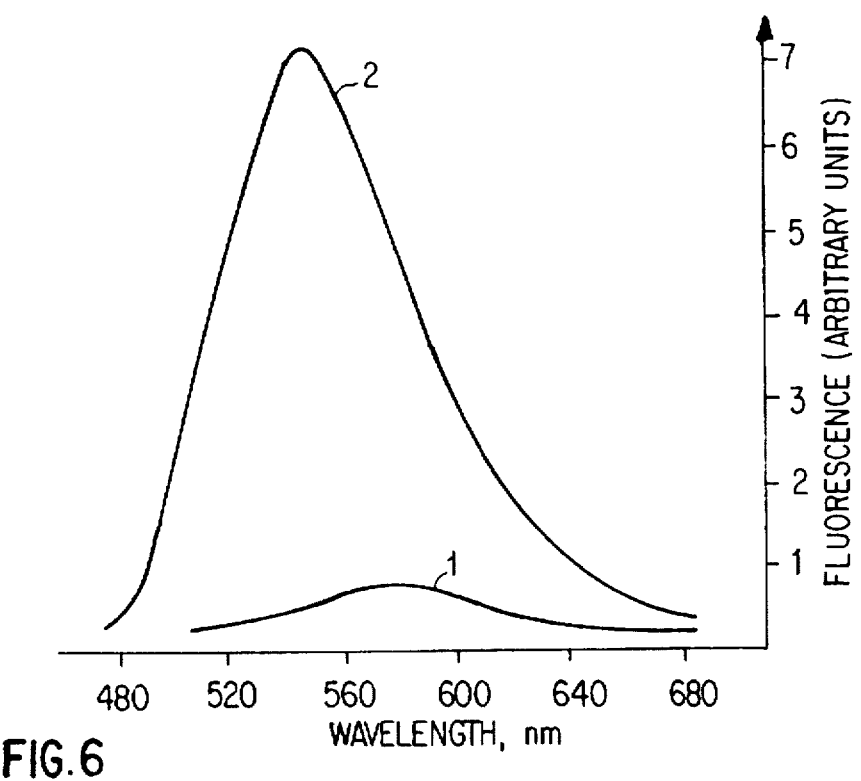
FIG. 6 is a plot of the fluorescence of DAP with TRITON X-100 (octyphenoxy polyethoxyethanol) in the solution as a function of wavelength. This figure shows that the peak fluorescence takes place at 550 nm. For comparison the (insignificant) fluorescence of DAP in the absence of TRITON X-100 (octylphenoxy polyethoxyethanol) is also shown.

The second part of the human blood serum sample was diluted 20 times by 0.05M phosphate buffer at pH 7.2. The experiment was repeated with the novel colorimetric method on the 20 times diluted human blood serum sample, i.e., 50 micro liters of the diluted blood serum were used. Such dilution is well beyond the sensitivity of the conventional ELISA. The first stages were identical to the commercial Roche kit. The washing was done differently. The procedure followed was the one described, see p. 9. above. Subsequently o-PD purified according to the description in Example 1 above was used. The irradiation too, was according to the irradiation procedure in Example 1, except that the irradiation was done in a test tube (and not in cuvette). The concentration of CEA was found to be 0.12 ng/ml. The commercial kit manufacturer states that its sensitivity limit for CEA is 0.5 ng/ml (FIG. 4a and 4b).

EXAMPLE 3

Determination of HRP Concentration in Solution by Fluorescence

Figure 7:
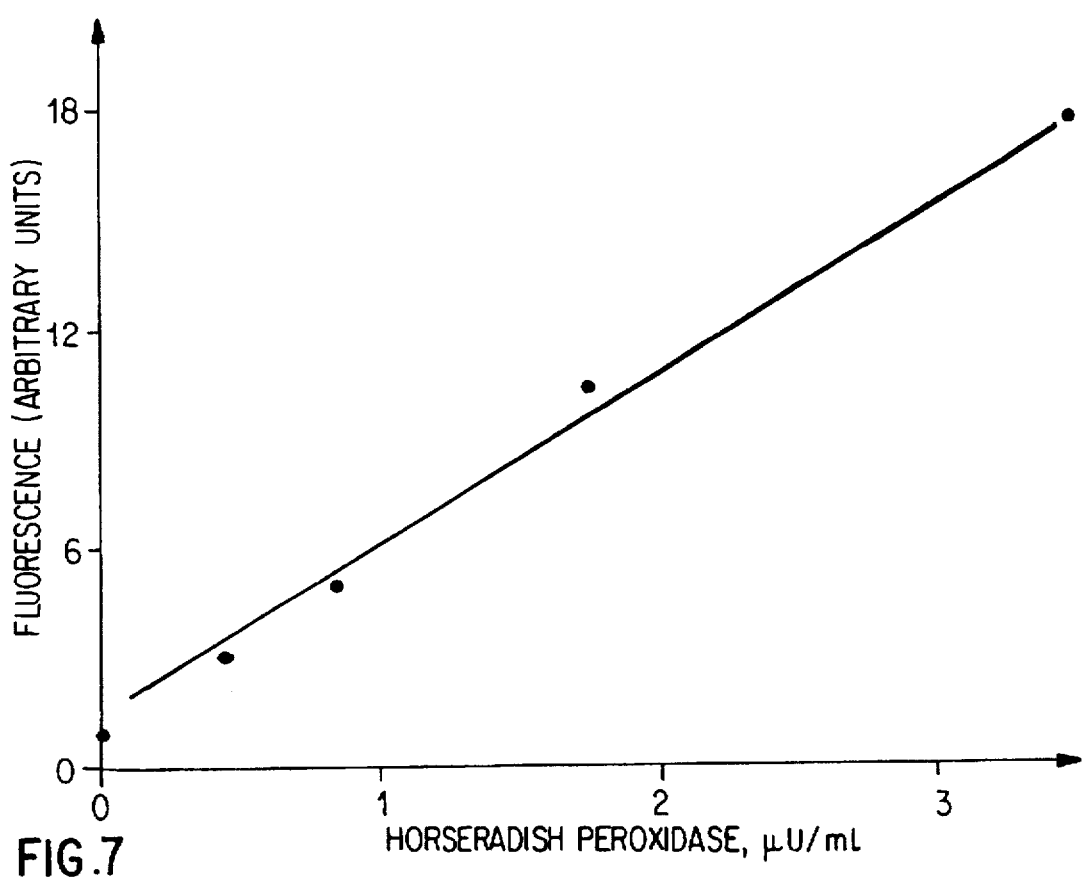
FIG. 7 is a plot of the fluorescence of DAP at 550 nm as a function of HRP activity.

The experiment was executed in the same manner as the photosensitive assay equivalent experiment in Example 1, except that after the completion of the enzyme reaction (i.e. instead of the irradiation in the equivalent photosensitive assay) TRITON X-100 (octylphenoxy polyethoxyethanol) was added and the fluorescence measured with a spectrofluorometer. The results are given in FIG. 7.

EXAMPLE 4

Determination of Carcinoembryonic Antigen (CEA) by Fluorescence

Figure 8:
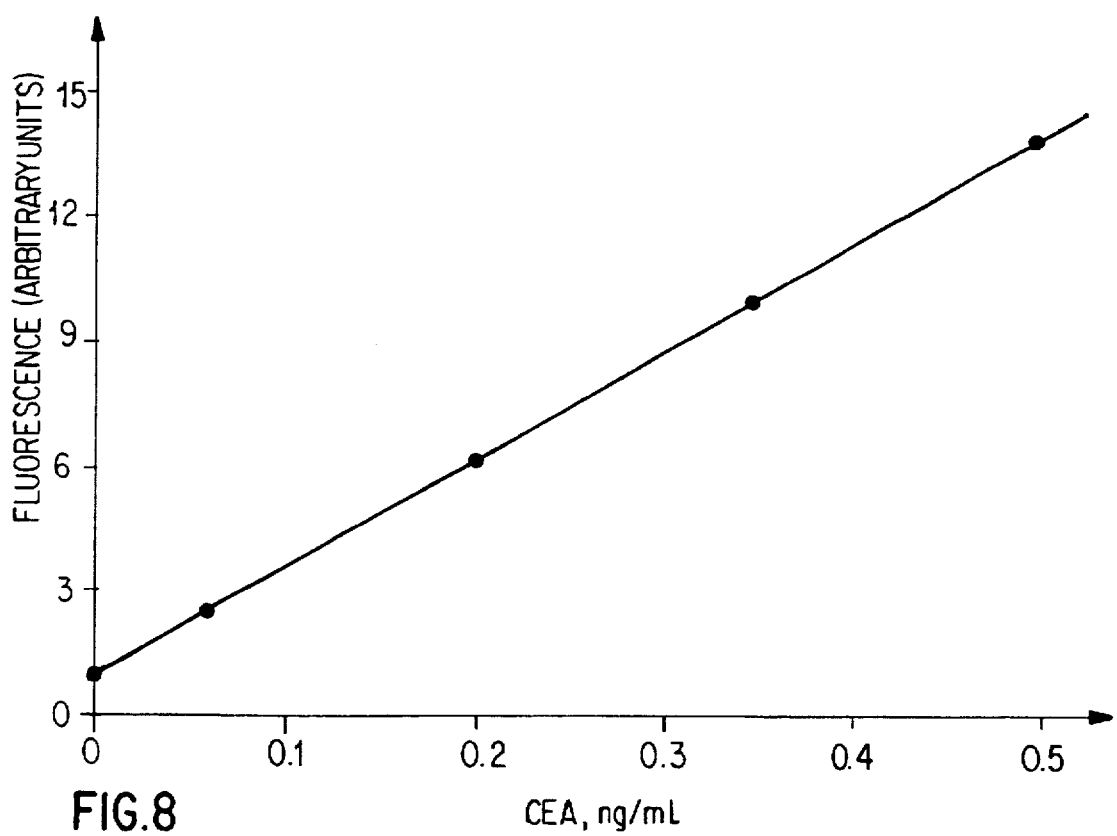
FIG. 8 is a plot of the fluorescence of DAP at 550 nm as a function of CEA concentration in the fluorescence enhanced assay.

The experiment was executed in the same manner as the photosensitive equivalent assay experiment in Example 2, except that here again the same changes as those explained in Example 3 in respect to Example 1 were introduced. The results are given in FIG. 8.

EXAMPLE 5

Calibration Curve of Octaldecylamideritrosine (ER18) in Dimyrostoylphosphatidylicholine (DMPC)

Figure 9:
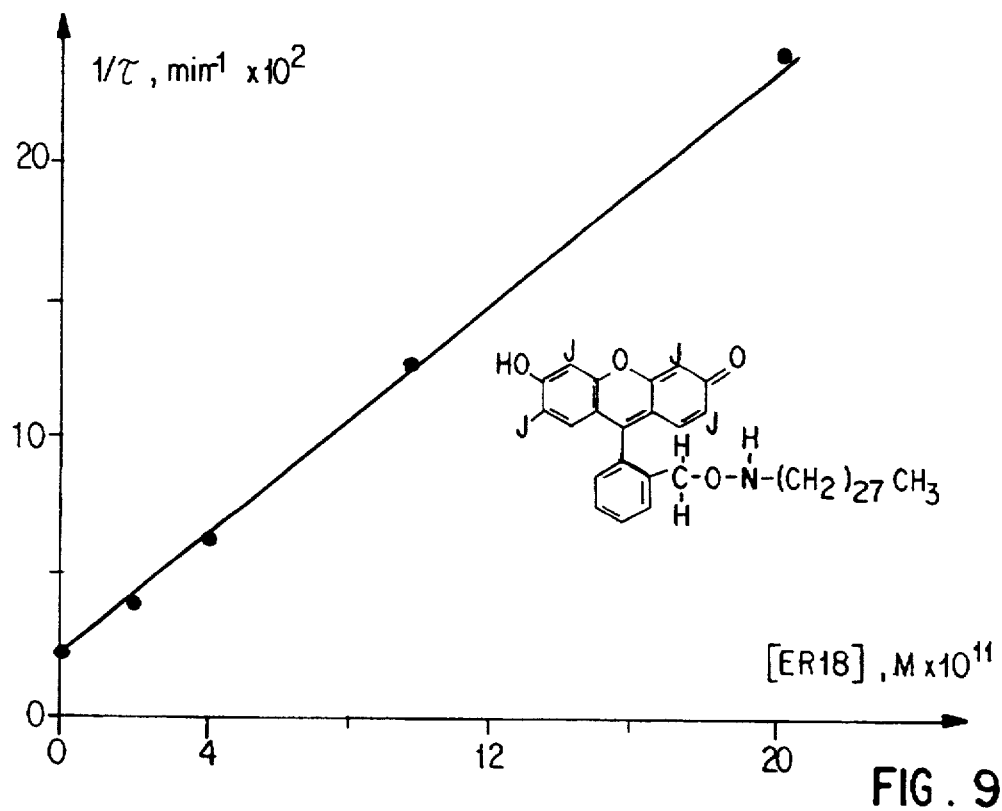
FIG. 9 is a plot of the rate of reaction as a function of a derivative of octadecylamid-erythrosin ER18 concentration.

To phosphate buffer of 0.1M and pH 7.2, 3.5 mg of dry DMPC is added. The mixture is heated to 40° C. and intensively shaken for 10 minutes. While this takes place, 0.01 ml of alcohol solution of $10^{-4}$M diphenulisobenzofuran (DPBF) are added. Solution is incubated for 10 minutes. Subsequently it is divided into 5 samples of 1 ml each. ER18 is introduced in concentrations of 0, $2\times10^{-11}$M, $5\times10^{-11}$M and $2\times10^{-11}$M respectively. Each sample is illuminated by 1,000 watts Hg lamp through filters which limit the wavelength to 540 nm. The procedure was repeated with each sample 4 times for each sample within one to 10 minutes and rate of reaction calculated (FIG. 9).

I claim:

1. A heterologous assay for the determination of an analyte in an aqueous sample which comprises:

binding a first entity having an affinity for the analyte to a solid support;

bonding the first entity with the analyte to form a complex;

reacting the first entity:analyte complex with a second entity, which is tagged by an enzyme, to produce a second entity:first entity:analyte complex;

contacting the second complex with oPD (orthophenylene-diamine) and $H_2O_2$ by which oPD is converted to DAP (2,3-diamino-phenazine);

irradiating the sample with light energy that includes radiation in the range of wavelengths from about 400 to about 500 nm, thereby initiating further production of DAP in the sample; and after irradiating, measuring to quantitate the analyte.

2. A process according to claim 1, further comprising adding TRITON X-100 before irradiating the sample and measuring to quantitate any resulting fluorescence with a spectrofluoromoter.

3. An assay according to claim 2, wherein the irradiation step is excluded and the production of further DAP occurs as a result of incubating the TRITON with the sample.

4. An assay according to claim 1, wherein the assay is part of a competitive immunoassay.

5. An assay according to claim 1, where the bound first entity is an antibody, the analyte bound thereto is an antigen, and the second entity is an enzyme-tagged antibody.

6. An assay according to claim 1, where the bound first entity is an antigen, the entity bound thereto is an antibody which is the analyte, and the second entity is an enzyme-tagged antibody.

7. An assay according to claim 1, wherein the analyte or the said first or second entity is selected from antigens, ligands, antibodies, receptors, and anti-isotypic antibodies, which interact with another entity which has a specific affinity therefor.

8. An assay according to claim 1, where the analyte is carcinoembryonic antigen (CEA), hepatitis-B virus, myoglobin, HIV-1 virus, HIV-2 virus, or insulin.

9. A kit for the quantitative determination of an analyte comprising an antigen by heterogeneous assay according to claim 1, which kit comprises in combination:

a) a monoclonal or polyclonal antibody against said antigen coated on a solid carrier, b) a second monoclonal or polyclonal antibody against the same antigen, wherein said second antibody is conjugated to horseradish peroxidase, c) a powder or tablet or purified oPD, d) a citrate-phosphate buffer containing hydrogen peroxide, and e) means for illumination of said sample by visible light in the range of 400–500 nm.

10. A kit according to claim 9, further comprising a diluent solution for the sample in buffered state and a buffered rinsing solution.

11. A kit for the quantitative determination of an analyte comprised of an antigen by heterogeneous assay according to claim 1, which kit comprises in combination:

a) a monoclonal or polyclonal antibody against said antigen coated on a solid carrier, b) a second monoclonal or polyclonal antibody against the same antigen, wherein said second antibody is conjugated to horseradish peroxidase, c) a powder or tablet or purified oPD, d) a citrate-phosphate buffer containing hydrogen peroxide, and e) a solution containing an octylphenoxy polyethoxyethanol surfactant.

* * * * *